United States Patent
Baek

(10) Patent No.: US 10,832,806 B1
(45) Date of Patent: *Nov. 10, 2020

(54) MEDICAL LABELING SYSTEM AND METHOD OF USE

(71) Applicant: Peter S. Baek, Southlake, TX (US)

(72) Inventor: Peter S. Baek, Southlake, TX (US)

(*) Notice: Subject to any disclaimer, the term of this patent is extended or adjusted under 35 U.S.C. 154(b) by 233 days.

This patent is subject to a terminal disclaimer.

(21) Appl. No.: 15/928,055

(22) Filed: Mar. 21, 2018

Related U.S. Application Data

(63) Continuation-in-part of application No. 15/346,622, filed on Nov. 8, 2016.

(60) Provisional application No. 62/474,411, filed on Mar. 21, 2017.

(51) Int. Cl.
| | |
|---|---|
| *G16H 20/10* | (2018.01) |
| *G06K 7/10* | (2006.01) |
| *G06K 7/14* | (2006.01) |
| *G06K 1/12* | (2006.01) |

(52) U.S. Cl.
CPC .............. *G16H 20/10* (2018.01); *G06K 1/121* (2013.01); *G06K 7/10297* (2013.01); *G06K 7/1413* (2013.01)

(58) Field of Classification Search
CPC ............ G06F 19/3462; G06F 19/3456; G06Q 10/087; G06K 2017/009; G06K 15/024; G06K 7/10297; G06K 7/1413; G06K 1/121; A61J 2205/30; G16H 20/10

USPC .......................................................... 705/2-3
See application file for complete search history.

(56) References Cited

U.S. PATENT DOCUMENTS

| | | | |
|---|---|---|---|
| 8,639,525 B2* | 1/2014 | Levine | G16H 20/17 |
| | | | 705/2 |
| 2009/0204255 A1* | 8/2009 | Yuyama | G16H 20/13 |
| | | | 700/225 |
| 2013/0092727 A1* | 4/2013 | Edwards | B65C 11/0289 |
| | | | 235/375 |
| 2014/0226180 A1* | 8/2014 | Alex | H04N 1/00519 |
| | | | 358/1.15 |
| 2015/0034713 A1* | 2/2015 | Jones | G06Q 50/22 |
| | | | 235/375 |
| 2015/0249770 A1* | 9/2015 | Delaney | G06F 3/1259 |
| | | | 358/3.28 |

* cited by examiner

*Primary Examiner* — Joy Chng

(57) ABSTRACT

A labeling system for creating labels for medicine containers. The system includes a label printer having an interior area configured to carry a plurality of printing sheets therein; a scanner in data communication with the label printer, the scanner having a reader to scan a drug administer barcode and a drug barcode; and a label sheet printed by the label printer, the label sheet having a plurality of labels adhesively bonded thereto, the label printer being configured to print onto the plurality of labels data information scanned from the administrator barcode and the drug barcode. The label sheet includes a first label having an image corresponding to a part of a body; and a second label having the image of the first label.

19 Claims, 14 Drawing Sheets

1601

1701

MEDICAL LABELING SYSTEM AND METHOD OF USE

BACKGROUND

1. Field of the Invention

The present invention relates generally to printing systems, and more specifically, to a printing system configured to print a plurality of labels for medicine containers.

2. Description of Related Art

It is known that anesthesiologist, doctors, nurses, and the like administer some of the deadliest medications to the patient during operation and recover. The drug administers sometimes work alone without consultations from other parties prior to and during the operation. Prior to the operation, conventional process of preparing the medications for operation includes handwriting the medicine type, dosage, date, and time are written on a wax-type paper. This process 101 is shown in FIG. 1, wherein the drug administer writes on an adhesively-backed wax label 103, which is then placed on the outer surface of the medicine bottle 105.

Conventional labeling methods, as depicted in FIG. 1, suffer from many drawbacks, and have limited reliability due primary to human error. For example, sloppy handwriting can make the label difficult to read, or altogether illegible. It should also be understood that each administer who prepares the label may also be doing so in a manner different from other administers, or attribute different meanings to the content of a label than another administers. This process is widely known and a common problem among anesthesiologist.

Accordingly, there is a need in the art for a labeling system compliant with medical standards that reduces, if not eliminates, human error during the labeling process.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
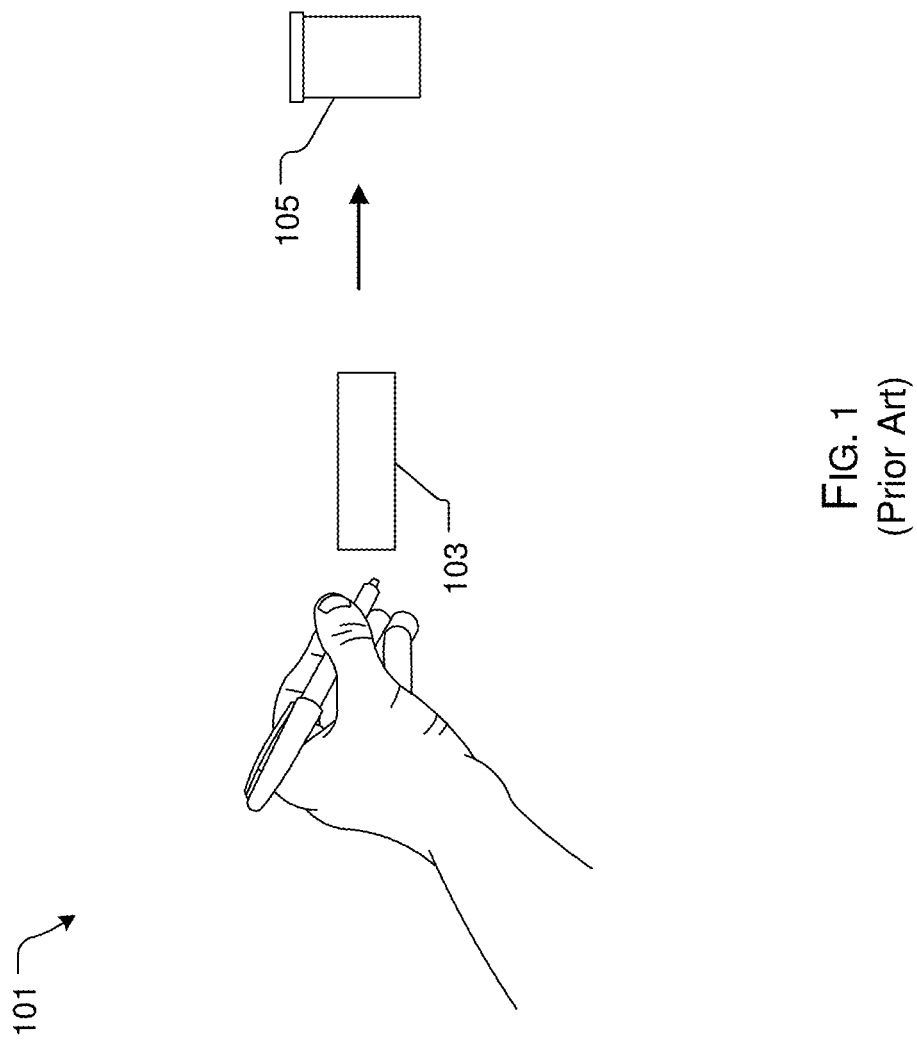
FIG. 1 is a simplified front schematic of a conventional process to create labels for medical containers.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional systems and methods of creating labels for medicine containers. Specifically, the system provides rapid and effective means to create and print a plurality of labels simultaneously, which in turn greatly reduces the time and effort to prepare the medicines for operation. The system and method also reduces, if not eliminates, human error due to legibility of the labels. The system is also adapted for use with a preprinted sheet of barcodes associated with a specific type of drug to be administer, which are scanned by the administer and the drug information printed on a sheet of labels. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
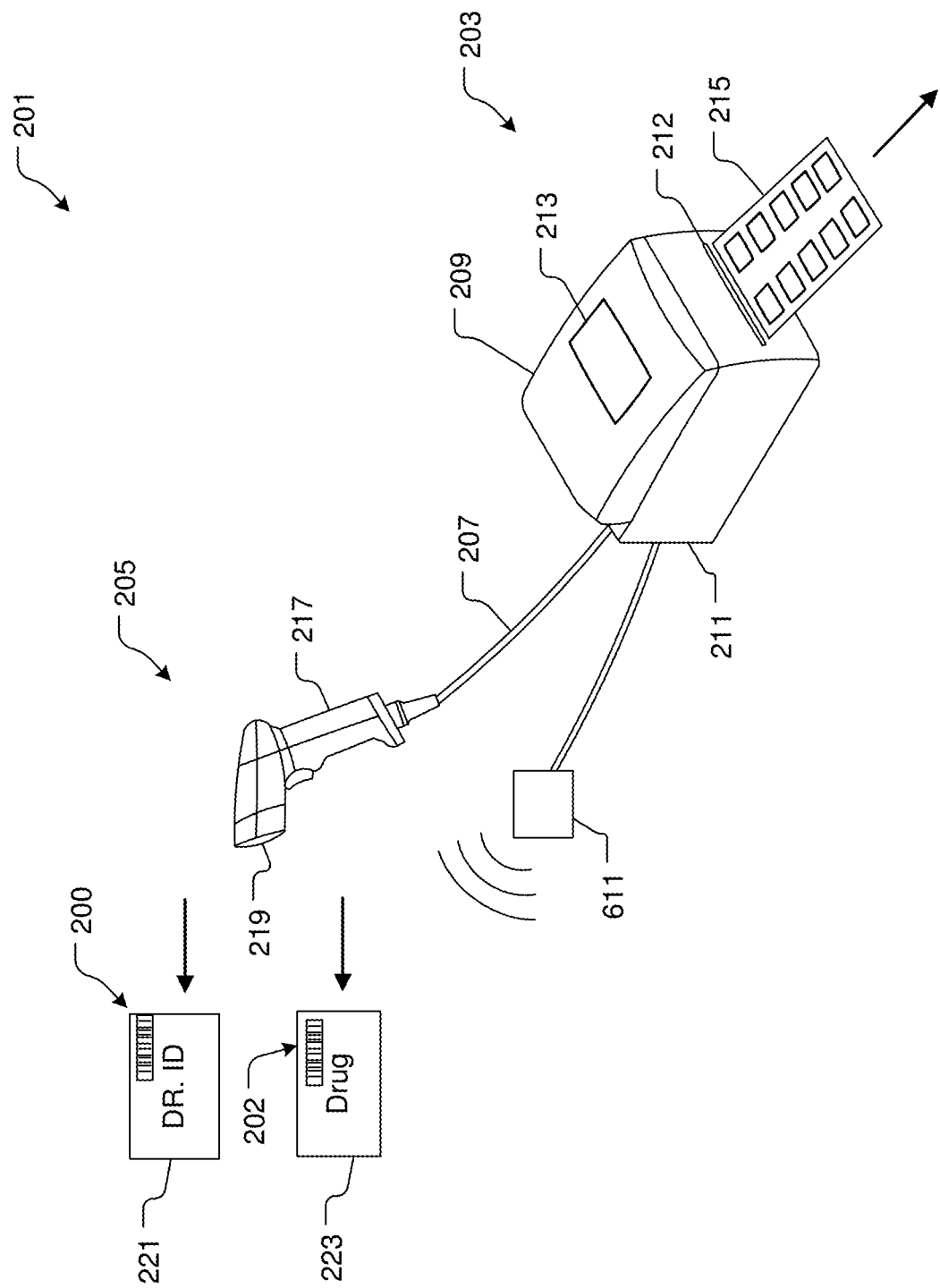
FIG. 2 is an oblique view of a labeling system in accordance with a preferred embodiment of the present application.

Referring now to the drawings wherein like reference characters identify corresponding or similar elements throughout the several views, FIG. 2 depicts an oblique view of a labeling system 201 in accordance with a preferred embodiment of the present application. It will be appreciated that the labeling system 201 overcomes one or more of the above-listed problems commonly associated with the conventional devices and methods for creating labels for medical containers, as will be discussed more fully below.

In the contemplated embodiment, system 201 includes a printer 203 operably associated with a scanner 205 and conductively connected thereto via a cord 207. Printer 203 includes a top 209 pivotally connected to a base 211 configured to carry a plurality of label sheets 215 therein. During use, the user can pivot open top 209 to position label sheets 215 within a cavity (not shown) formed by base 211. The label sheets 215 are fed through a printing device (not shown) disposed within base 211 and exit through an opening 212 where they are then accessible to the user.

Printer 203 is further provided with a display 213 carried on top 209 and in viewing access to the user. In one contemplated embodiment, the display 213 merely displays information related to creating the labels, for example, Doctor Information, medicine information, date, time, dosage, expiration, and so forth. In an alternative embodiment, display 213 is manipulated by the user, for example, the display is touch sensitive, thereby allowing the user to manually input information. The display 213 could also be configured to read finger prints for security verification prior to use.

Although not shown, printer 203 includes one or more ports that allows communication with a computer for pre-programming. Also, in the contemplated embodiment, the printer 203 includes a power cord (not shown) that provides electrical energy to printer 203 via an electrical outlet.

One of the unique features believed characteristic of system 201 is the use of a scanner 205 used to obtain information for printing the labels on sheet 215. This features greatly reduces the time and effort to create medical labels for containers, and potentially eliminates the human error during the process.

Figure 8:
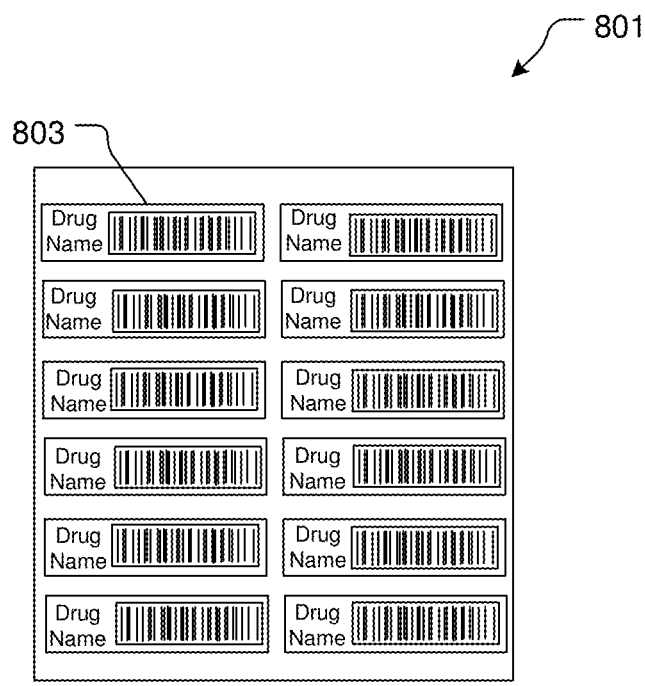
FIG. 8 is a front view of a drug identifier sheet.

Scanner 205 includes a handle 217 integrally attached to a reader 219. During use, the user will hold handle 217 and scan, for example, a barcode 200 associated with the doctor's identification 221 and a barcode 202 associated with the type of medicine being used, as indicated by box 223. It should be understood that the majority of medicine bottles include barcodes adhered to the bottle, which provide important medical information. Thus, box 223 could represent a barcode directly from the medicine bottle. Further, it is contemplated obtaining the drug information from a sheet 801 of labels having different types of drug information, as depicted in FIG. 8.

Figure 3:
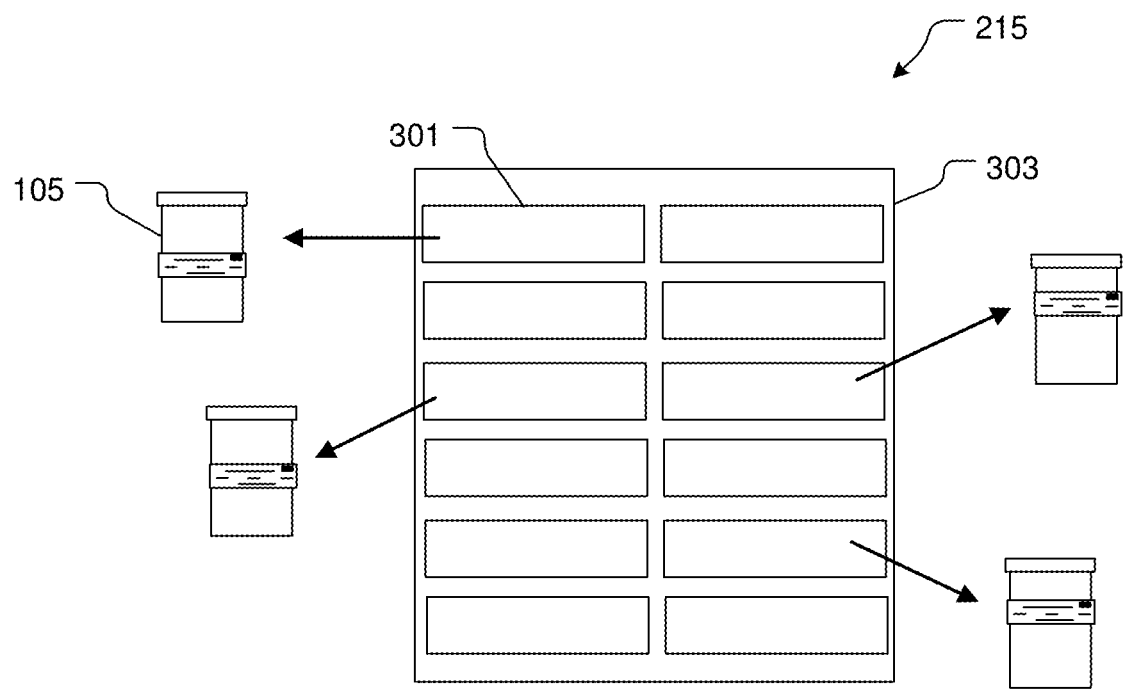
FIG. 3 is a front view of a label sheet of the labeling system of FIG. 2.

Referring now to FIG. 3, a simplified front view of a label sheet 215 is shown having a plurality of medical labels 301 adhesively bonded to a sheet 303. Another unique feature believed characteristic of system 201 is the ability to print a plurality of labels 301 simultaneously, thereby greatly reducing the time and effort to create the labels. During use, a plurality of label sheets 215 are placed in the cavity of base 211 and thereafter fed through a printer device and the drug and doctor information from scanner 205 is placed on individual labels 301. The user then removes labels 301 from sheet 303 and adhesively adheres the labels to bottles 105. In some embodiments, the label sheet could include one or more labels 301 that are blank, which in turn the user can handwrite information directly to the labels 301.

Figure 4:
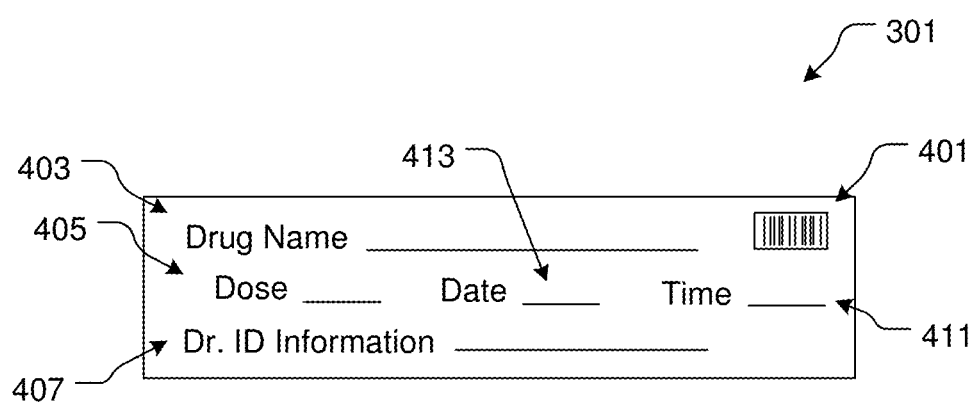
FIG. 4 is a front view of a medical label of the label sheet of FIG. 3.

As depicted in FIG. 4, subject matter such as the Doctor's information, medicine information, dosage, time, date, and an optional bar code can be printed to the label 301 via printer 203. Specifically, the label 301 includes a barcode printed on section 401, the drug name printed on section 403, the dose printed on section 405, the administers information printed on section 407, the time printed on section 411, and the date printed on section 413.

Figure 5:
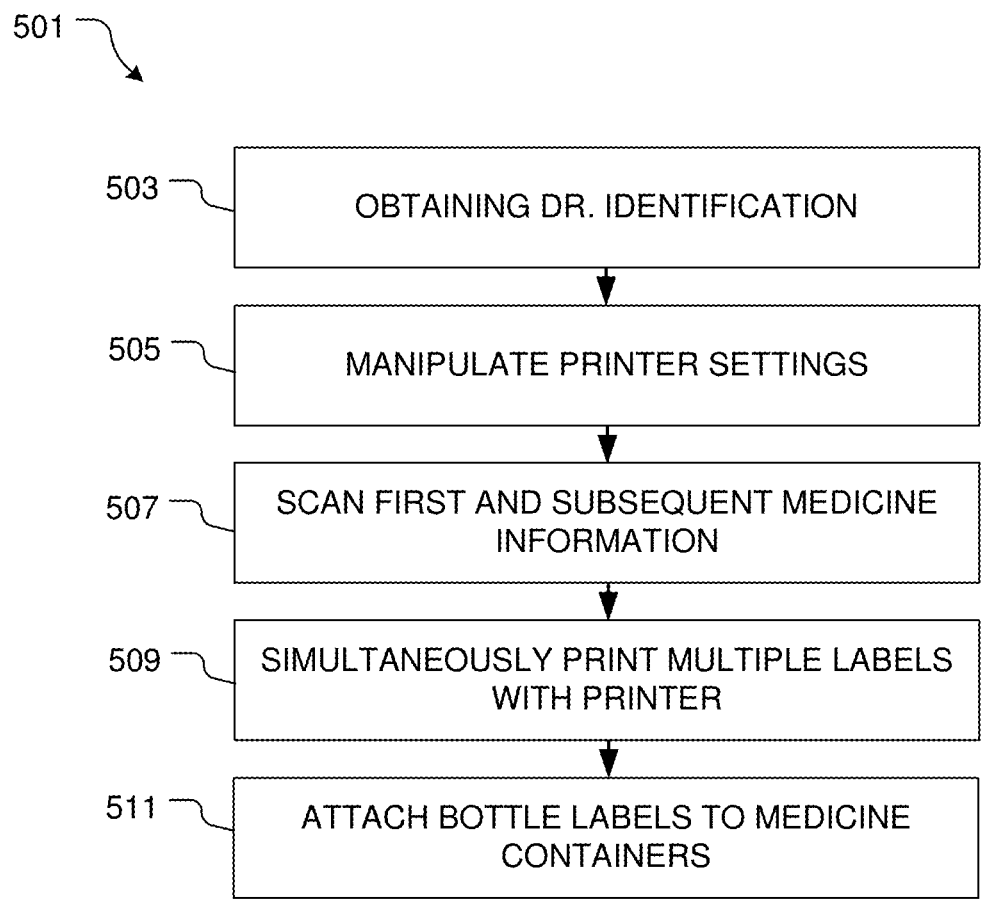
FIG. 5 is a flowchart of the labeling method in accordance with a preferred embodiment of the present application.

In FIG. 5, a simplified flowchart 501 depicting the preferred process is shown. The process starts with obtaining the Doctor's information, which can be achieved via scanner 205, a radio-frequency identification (RFID) badge, or the like, as indicated by box 503. After the Doctor's information is received, the printer settings are manipulated, as indicated by box 505. For example, the user may wish to switch between child and adult medicine dosages, blank labels, and the like. Next, the user scans the barcodes associated with the various types of medicines to be adhered during operation, as indicated by box 507. Thereafter, the printer simultaneously prints the plurality of labels on label sheet 215, as indicated by box 509. Lastly, the individual labels 301 are removed from sheet 303 and placed on bottles 105, as indicated by box 511.

Figure 6:
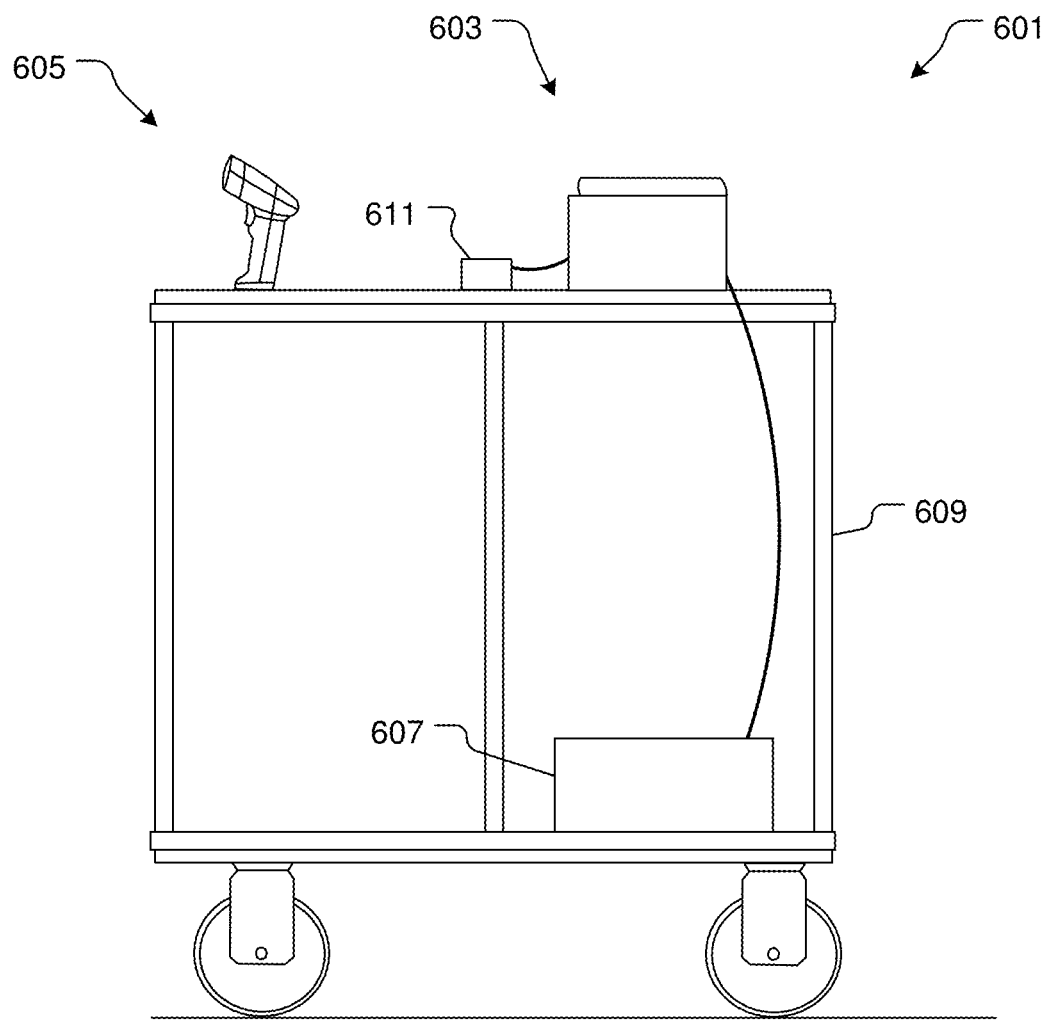
FIG. 6 is a side view of a labeling system in accordance with an alternative embodiment of the present application.

It will be appreciated that alternative embodiments are also contemplated. In FIG. 6, a side view of a printer system 601 is shown in accordance with an alternative embodiment. System 601 is substantially similar in form and function to system 201 and incorporates one or more of the features discussed above, and vice-versa.

System 601 includes a printer 603 operably associated with a wireless scanner 605 and conductively coupled to a battery system 607. As shown, the components of system 601 are carried on a cart 609, which in turn increases the mobility of system 601 during use. One additional feature of system 601 includes a RFID reader 611 configured to wirelessly read information, e.g., the doctor's badge having a RFID tag, during use.

Figure 7:
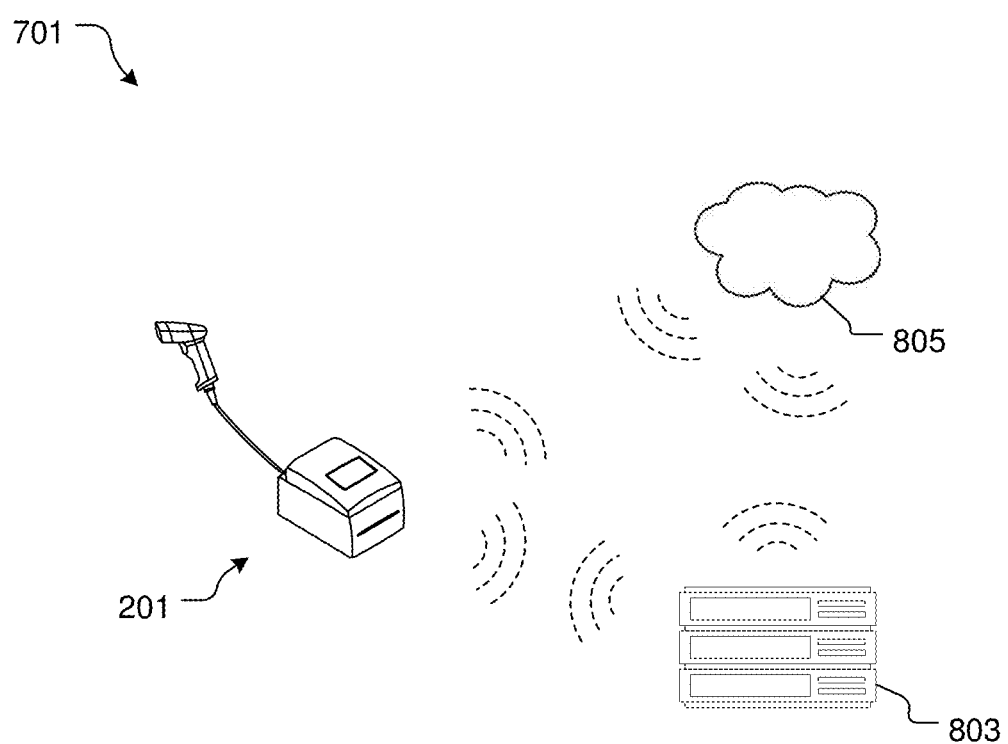
FIG. 7 is a side view of a labeling system in accordance with an alternative embodiment of the present application.

Referring to FIG. 7 in the drawings, a simplified schematic of a labeling system 701 is shown in accordance with an alternative embodiment. System 701 is substantially similar in form and function to the systems discussed above and incorporates one or more of the features discussed herein, and vice-versa.

In the contemplated embodiment, system 701 includes the features of system 201 operably associated with a database 803 and cloud service 805. Accordingly, the data obtained from system 201 can be reviewed and programmed via database 803 and/or cloud service 805. In the exemplary embodiment, the system 201 communicates with database 803 and/or cloud 805 wirelessly. This feature allows the printer to received up-to-date information regarding each type of medicine being used and for other third parties to review the medicines being used by the user during operation. Although not shown, system 201 could include transceivers and other devices that allow communication with database 803 and/or cloud service 805.

Referring now to FIG. 8, a front view of a drug label sheet 801 is shown. In the contemplated embodiment, the drug label sheet 801 contains information about the particular type of drug being administered to the patient. The sheet 801 includes a plurality of boxes, e.g., boxes 803 having information for different types of drugs, which in turn are scanned via scanner 219. After the bar codes are scanned via scanner 219, one or more labels 901 are printed on a sheet, for example, sheet 215 printed by printer 203.

Figure 9:
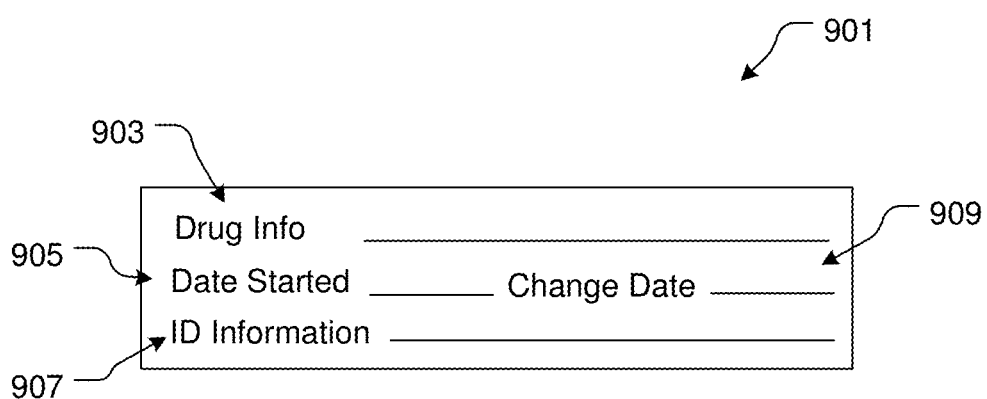
FIG. 9 is a label from a label sheet of the labeling system of FIG. 2.

FIG. 9 illustrates an exemplary label 901 created by scanning box 803. In the exemplary embodiment, the bar code of box 803 provides drug information, which is printed on section 903. The printer is preprogrammed with a date and time, which is printed on section 905. The process discussed above also captures the information from the doctor, nurse, and/or other party administering the drug; this information being printed on section 907.

One of the points of novelty believed characteristic of the process of creating label 901 is providing the change date that the drug being administered needs to changed. For example, it is well known that drugs have an expiration date, which requires the administer to interchange the drug prior to the expiration else the drug becomes useless and/or harmful to the patient. Accordingly, the label 901 has a section 909 that provides the administer the date for drug replacement.

Figure 10:
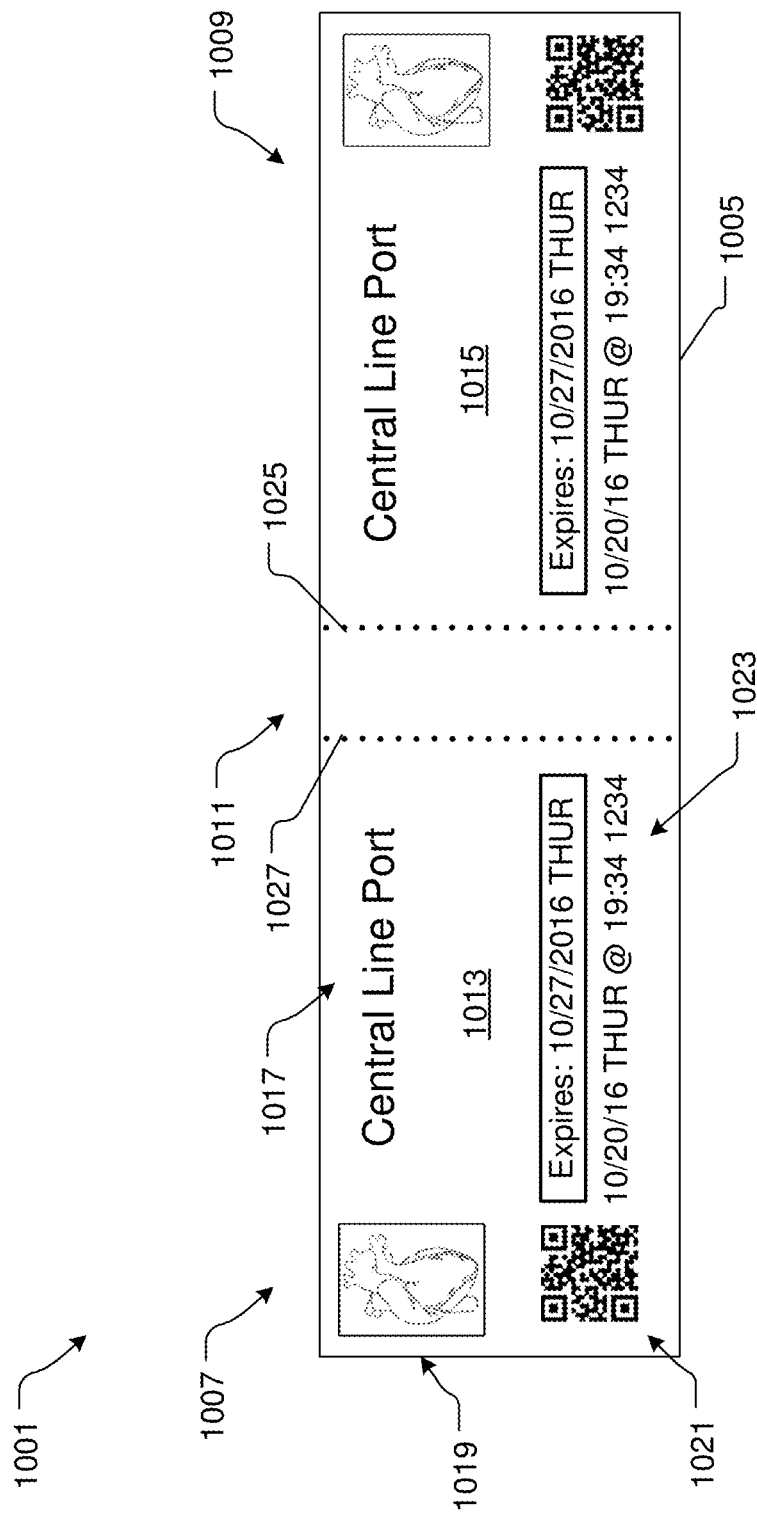
FIG. 10 is a front view of a label in accordance with an alternative embodiment of present application.
Figure 11:
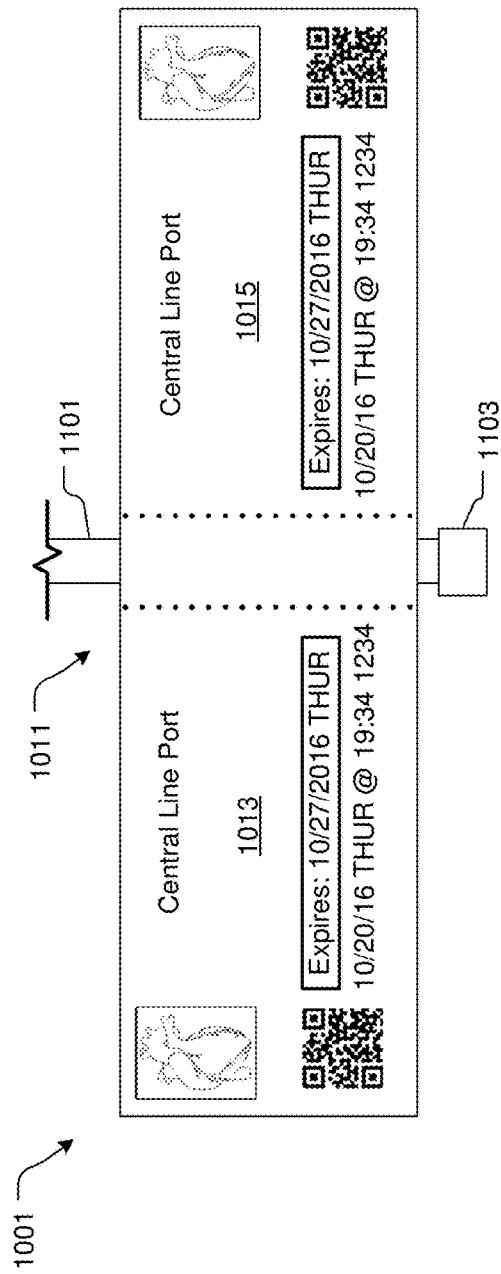
FIGS. 11 and 12 are front views of the label of FIG. 10 secured to a tube.
Figure 12:
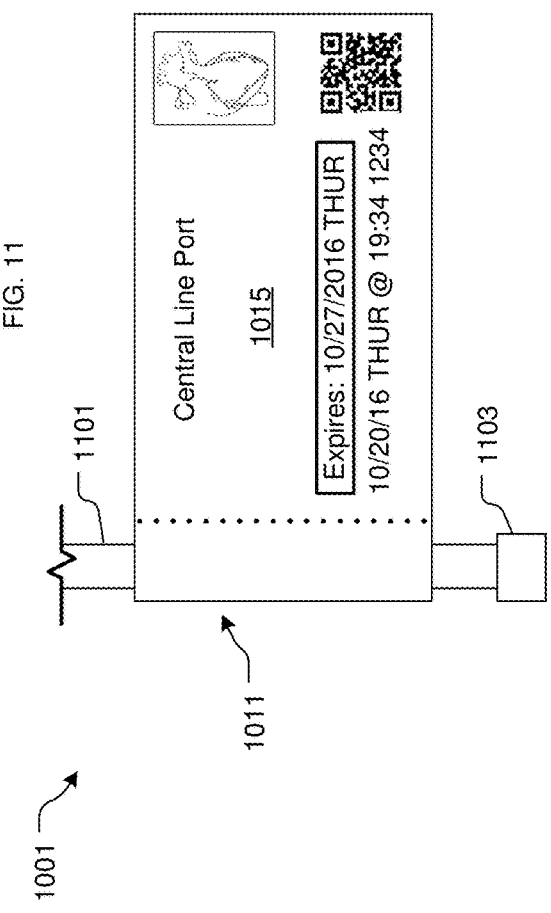

Referring now to FIGS. 10-12, an alternative embodiment of the labeling system 201 is shown. It will be appreciated that labeling system 1000 is substantially similar in form and function to system 201 and incorporates one or more features discussed above. In the exemplary embodiment, system 1000 utilizes a different type of label, but also utilizes the unique features of the portability of carrying out the label printing process discussed above.

System 1000 includes an unique label 1001 having a body 1005 with two opposing sections 1007, 1009 joined together via an intermediary section 1011. It should be understood that sections 1007 and 1009 include the same information on respective from surfaces 1013, 1015. A back surface of body 1005 (not shown) has an adhesive backing for securing the label to a tube 1101 about the intermediary section 1011.

Referring specifically to the printed content information on front surfaces 1013, 1015, it is contemplated having: a first printing 1017 indicating the type of port and corresponding tube the label is secured to; a QR code 1021 for scanning information, e.g., patient name, drug time, expiration time, and so forth; and a second printing 1023 that includes expiration dates and time along with patient information such as the patient's name. It will be appreciated that more or less printing is contemplated in alternative embodiments.

Figure 13:
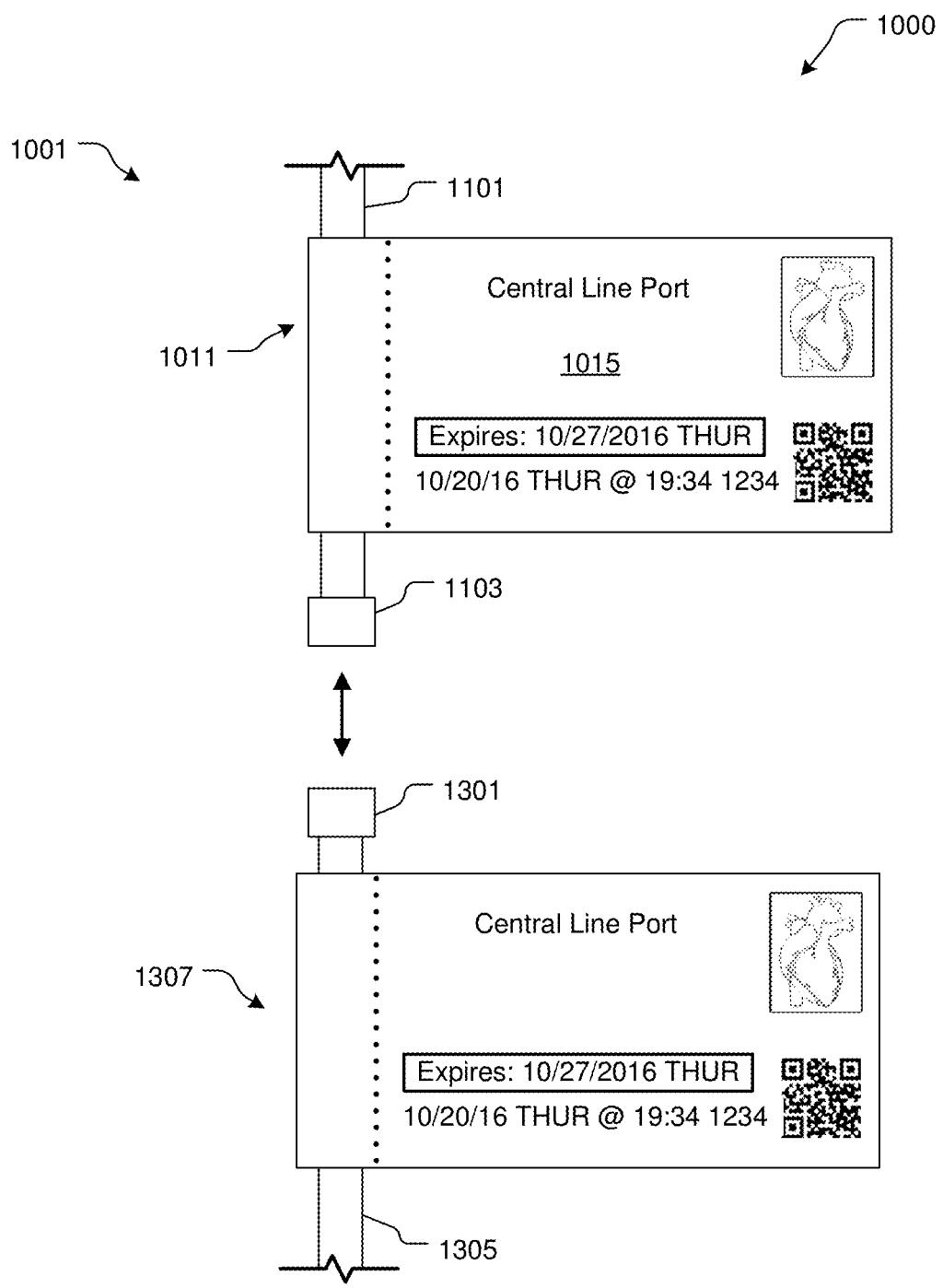
FIG. 13 is a front view of the labeling system in accordance with an alternative embodiment.
Figure 14:
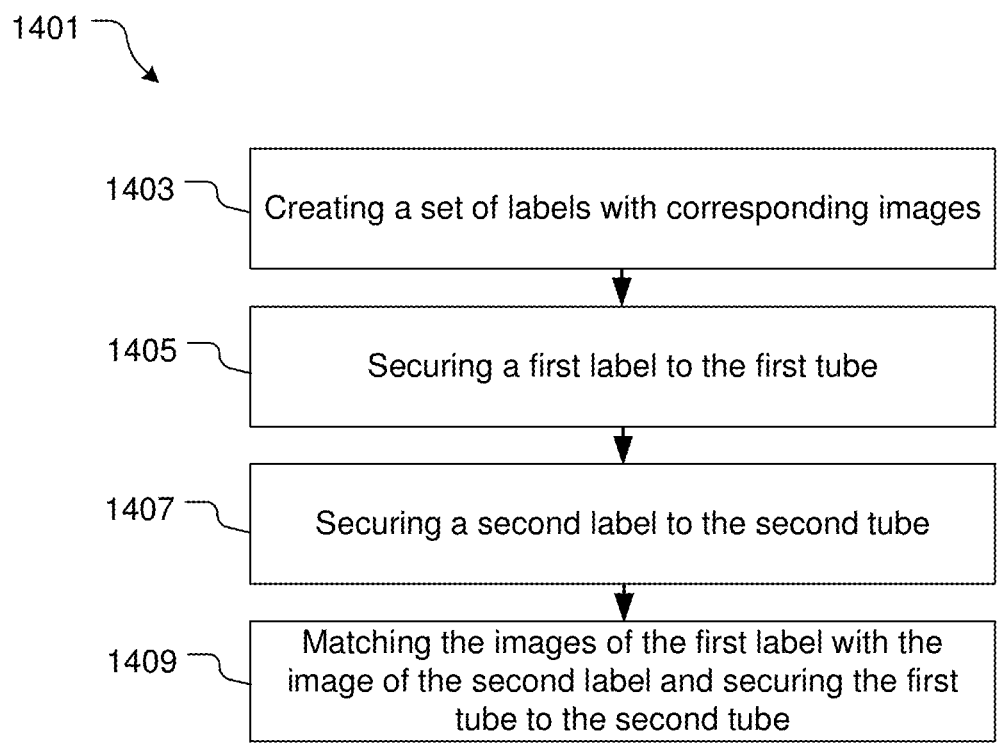
FIG. 14 is a flowchart of the labeling method in accordance with the alternative embodiment of the present application.

One of the points of novelty believed unique to the present invention is the use of an image 1019 that corresponds to areas being administered. For example, if the drugs are being applied to the heart, an image of the heart is shown. Likewise other images such as the stomach, lungs, liver, and so forth could be utilized. As depicted in FIG. 13, images from the labels must match images from adjoining tubes to provide a visual assurance that the two joining tubes are correct. It should be understood that medicine for the stomach could potentially kill a patient if received by the heart. Accordingly, the images provided on the label provide rapid and easily visual means to prevent the wrong tubes being joined.

An optional feature includes the option of creating two perforated lines 1025, 1027 that extend the width of the body 1005 and provide effective means for the body 1005 to wrap around the tube 1101, as depicted in FIGS. 11 and 12. Thereafter, the back surface of the body 1005 is adhesively secured. The tube 1101 includes an elongated hollow body with a fastener 1103 configured to engage with a fastener 1301 of joining tube 1305, as depicted in FIG. 13. In the contemplated embodiment, the fasteners are quick-release devices.

Flowchart 1401 depicts the preferred process of utilizing system 1000, which includes the steps of creating the set of label in accordance to system 201 and/or other similar means. Thereafter, the first label and the second label are secured to respective first tube and second tube configured to engage with each other. Prior to securing the tubes together, the images on each label secured to each tube are matched. These steps are outlined in boxes 1403, 1405, 1407, and 1409.

Although the features of system 1000 are discussed with reference to medical procedures, it will be appreciated that the features discussed herein could be utilized with other systems requiring the matching of joining hoses.

Referring now to FIGS. 14-18 in the drawings, a method of use is shown in accordance with a preferred embodiment of the present invention. It will be appreciated that the method discussed herein is operably associated with one or more system and devices discussed above. It should be understood that traditional printing of labels using a computer is a multi-step process that involves selecting the specific label, opening that file, choosing to print that file, selecting the appropriate printer, selecting the number of copies, and then pressing print. If a user wants to print 10 different labels, it requires a lot of button pushes and multiple steps.

Figure 15:
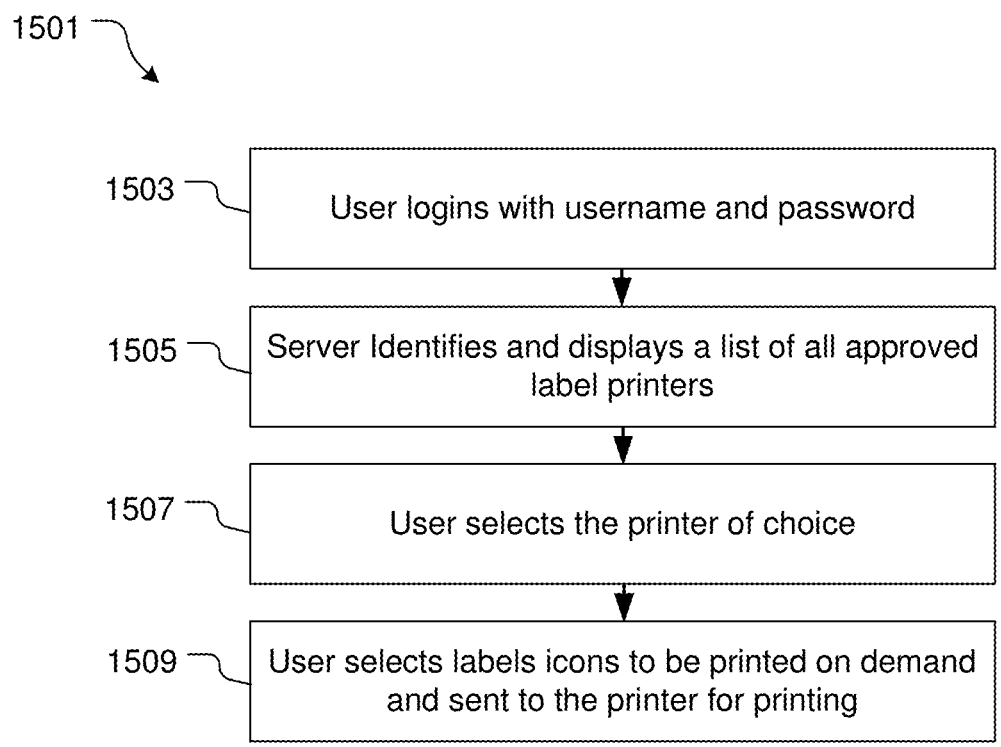
FIG. 15 is a flowchart of the labeling method in accordance with the alternative embodiment of the present application.
Figure 16:
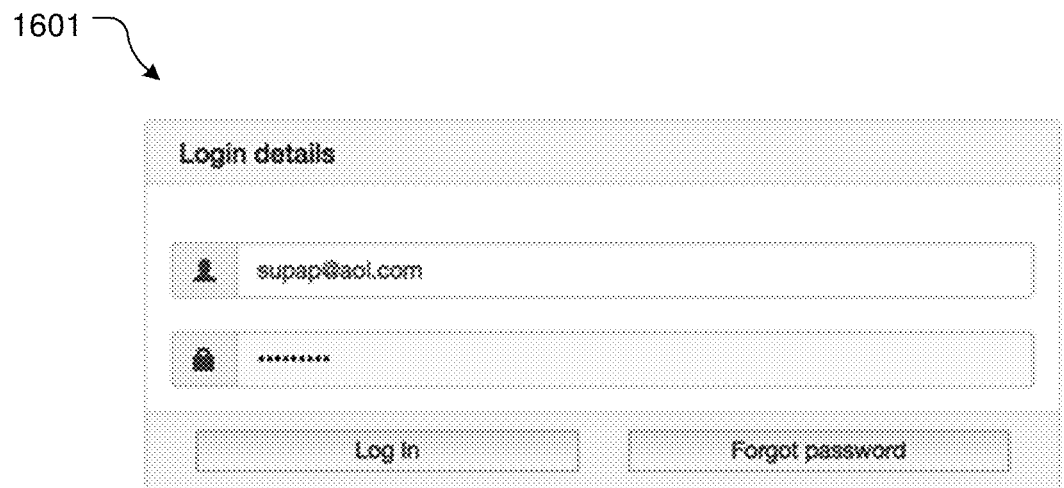
FIGS. 16, 17, and 18 are screenshots of a display of the present invention.
Figure 17:
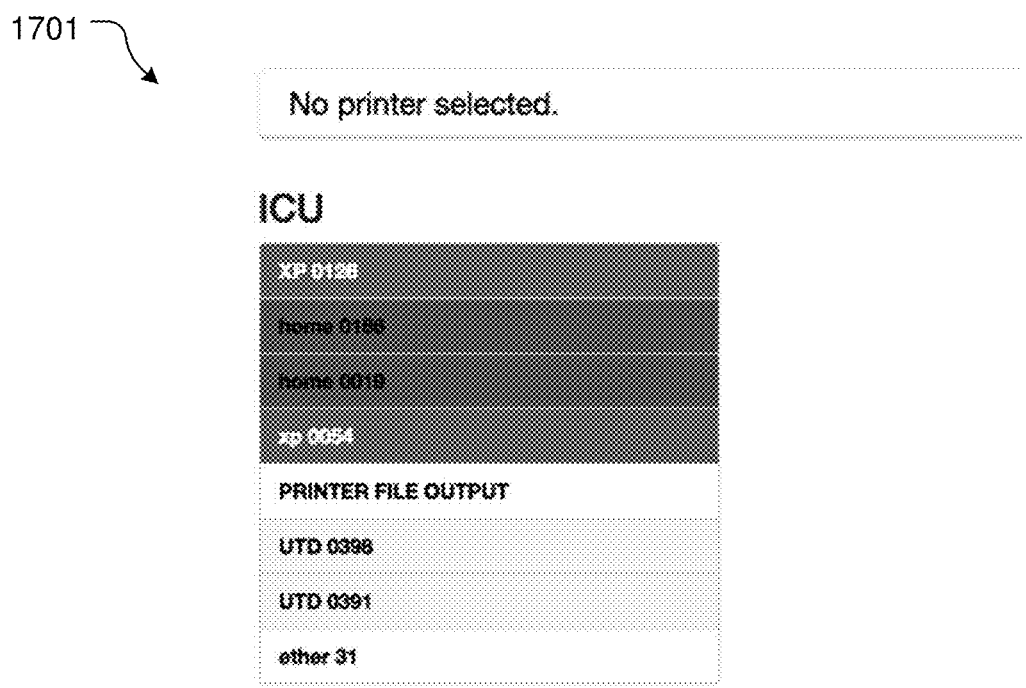
Figure 18:
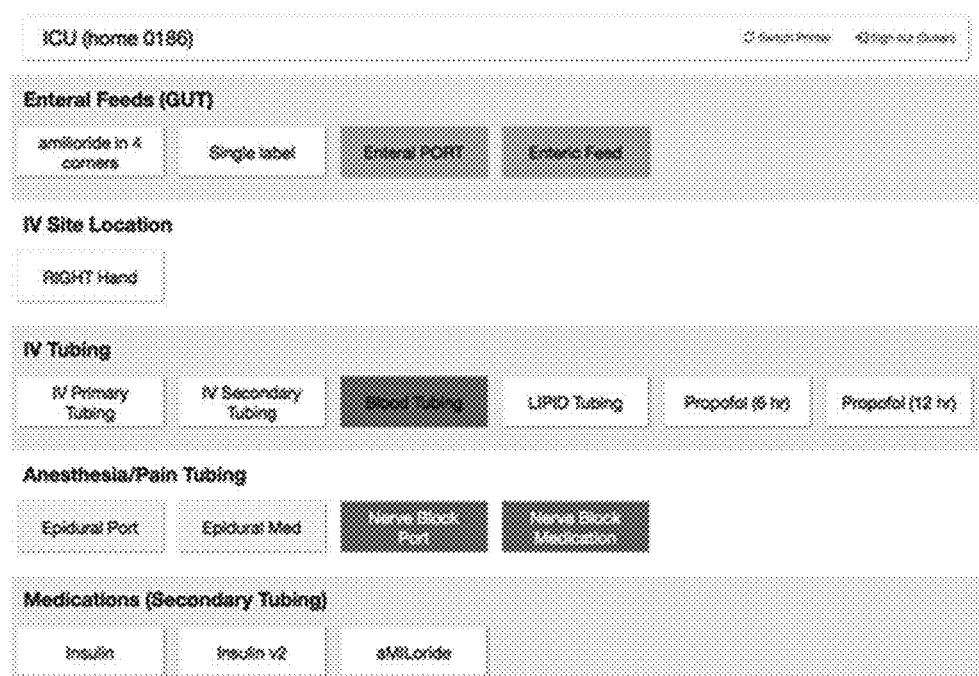

The method of the present invention simplifies problems commonly associated with conventional methods. Specifically, the method minimizes all those steps and makes it easy to print standardized, centrally controlled, completely up-to-date, 100 percent legible labels easily and efficiently with minimal effort. FIG. 15 shows a flowchart 1501 that depicts these features. Specifically, the user logins with a username and password into a central server of a computer, as depicted in box 1503. Thereafter, the server identifies the labels for printing, which in turn are selected by the user for printing, as depicted by box 1507. Finally, the printer prints the selected labels, as depicted in box 1509. As depicted, FIG. 16 illustrates a screenshot 1601 of the process of box 1503; FIG. 17 illustrates a screenshot 1701 of the process of boxes 1505, 1507; and FIG. 18 illustrates a screenshot 1801 of the process of box 1509.

It should appreciated that the method discussed herein can be applied for restaurants, warehouses, shipping, and so forth wherein any business or location that needs complete control of standardized information to be easily and simply printed. The features discussed herein could work on any web browser (PC/smartphone, ipad, etc). iOS and ANDROID apps.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A labeling system for creating labels for medicine containers, comprising:
   a label printer having an interior area configured to carry a plurality of printing sheets therein;
   a scanner in data communication with the label printer, the scanner having a reader to scan a drug administer barcode and a drug barcode; and
   a label sheet printed by the label printer, the label sheet having a plurality of labels adhesively bonded thereto, the label printer being configured to print onto the plurality of labels data information scanned from the administrator barcode and the drug barcode, the label sheet having:
      a first label having an image corresponding to a part of a body; and
      a second label having the image of the first label
   wherein the first label is secured to a first tube and the second label is secured to a second tube; and
   wherein the first tube is joined to the second tube.

2. The system of claim 1, further comprising:
   a RFID tag reader operably associated with the label printer, the RFID tag reader being configured to wirelessly obtain the administer information from a RFID tag.

3. The system of claim 1, further comprising:
   a drug barcode sheet having a plurality of barcodes for different types of drugs;
   wherein the scanner is configured to scan the barcodes for printing the label sheet via the printer.

4. The system of claim 1, further comprising:
   a cart for carrying the label printer and the scanner.

5. The system of claim 4, further comprising:
   a portable power supply carried on the cart and conductively coupled to the label printer.

6. The system of claim 1, the label printer further comprising:
   a display configured to display the drug administer information and the drug information.

7. The system of claim 6, wherein the display is a touchable display manually manipulated by the drug administer.

8. The system of claim 1, further comprising:
   a cloud server in data communication with the label printer; and
   a database in data communication with the cloud server;
   wherein the cloud server obtains information printed via the label printer; and
   wherein the information obtained by the cloud server is stored in the database.

9. A labeling system for creating labels for medicine containers, comprising:
   a label printer having an interior area configured to carry a plurality of printing sheets therein;
   a scanner in data communication with the label printer, the scanner having a reader to scan a drug barcode;
   a RFID reader in data communication with a RFID carried by a drug administer; and
   a label sheet printed by the label printer, the label sheet having a plurality of labels adhesively bonded thereto, the label printer being configured to print onto the plurality of labels data information scanned from the drug barcode, the label sheet having:
      a first label having an image corresponding to a part of a body; and
      a second label having the image of the first label;
   wherein the first label is secured to a first tube and the second label is secured to a second tube; and
   wherein the first tube is joined to the second tube.

10. The system of claim 9, further comprising:
    a drug barcode sheet having a plurality of barcodes for different types of drugs;
    wherein the scanner is configured to scan the barcodes for printing the label sheet via the printer.

11. The system of claim 9, further comprising:
    a cart for carrying the label printer and the scanner.

12. The system of claim 11, further comprising:
    a portable power supply carried on the cart and conductively coupled to the label printer.

13. The system of claim 9, the label printer further comprising:
    a display configured to display the drug administer information and the drug information.

14. The system of claim 13, further comprising:
    two elongated perforated lines extending the width of the label.

15. The system of claim 9, further comprising:
    a cloud server in data communication with the label printer; and
    a database in data communication with the cloud server;
    wherein the cloud server obtains information printed via the label printer; and
    wherein the information obtained by the cloud server is stored in the database.

16. A method to print labels, comprising:
    providing a computer with a central server for user access;
    imputing a username and password;
    selecting a set of labels in accordance to the system of claim 1 for printing; and
    printing the set of labels via a printer.

17. The method of claim 16, further comprising:
    securing the first label to the first tube;
    securing the second label to the second tube;
    matching the image of the first label with the image of the second label; and
    securing the first tube to the second tube.

18. The method of claim 17, further comprising:
    bending the first label around a periphery of the first tube via a perforated line.

19. The method of claim 17, further comprising:
    securing the first tube to the second tube via a quick-release device.

* * * * *